(12) United States Patent
Zaman et al.

(10) Patent No.: US 7,362,450 B2
(45) Date of Patent: Apr. 22, 2008

(54) SPECULAR SURFACE FLAW DETECTION

(75) Inventors: Kamran Zaman, Pittsford, NY (US); Dante Pietrantoni, Rochester, NY (US); Ken Gottschalk, West Henrietta, NY (US); Stanley Pietrzykowski, Brighton, NY (US)

(73) Assignee: Xerox Corporation, Norwalk, CT (US)

( * ) Notice: Subject to any disclaimer, the term of this patent is extended or adjusted under 35 U.S.C. 154(b) by 33 days.

(21) Appl. No.: 11/318,103

(22) Filed: Dec. 23, 2005

(65) Prior Publication Data

US 2007/0146691 A1 Jun. 28, 2007

(51) Int. Cl.
*G01B 11/30* (2006.01)

(52) U.S. Cl. .................. 356/600; 356/237.2; 356/612

(58) Field of Classification Search ............... 356/600, 356/612, 613, 237.2
See application file for complete search history.

(56) References Cited

U.S. PATENT DOCUMENTS

| | | | |
|---|---|---|---|
| 4,185,921 A | 1/1980 | Godai et al. | |
| 4,715,709 A | 12/1987 | Sekine et al. | |
| 4,794,264 A | 12/1988 | Quackenbos et al. | |
| 4,794,265 A | 12/1988 | Quackenbos et al. | |
| 4,853,777 A * | 8/1989 | Hupp | 356/613 |
| 4,929,846 A * | 5/1990 | Mansour | 356/613 |
| 5,086,232 A * | 2/1992 | Maguire et al. | 356/613 |
| 5,125,741 A | 6/1992 | Okada et al. | |
| 5,127,726 A | 7/1992 | Moran | |
| 5,153,844 A * | 10/1992 | Beni et al. | 356/613 |
| 5,225,890 A * | 7/1993 | Lee et al. | 356/613 |
| 5,557,402 A | 9/1996 | Osawa et al. | |
| 5,815,773 A | 9/1998 | Zaman | |
| 6,046,801 A | 4/2000 | Liu et al. | |
| 6,373,565 B1 | 4/2002 | Kafka et al. | |
| 6,603,542 B1 | 8/2003 | Chase et al. | |
| 6,963,076 B1 | 11/2005 | Zaman et al. | |
| 7,099,002 B2 * | 8/2006 | Ishiura et al. | 356/237.2 |
| 2005/0202330 A1 | 9/2005 | Tong et al. | |

FOREIGN PATENT DOCUMENTS

| | | |
|---|---|---|
| JP | 07-128240 | 5/1995 |
| JP | 07-128241 | 5/1995 |
| JP | 09-325120 | 12/1997 |

\* cited by examiner

*Primary Examiner*—Layla G. Lauchman
*Assistant Examiner*—Juan D Valentin
(74) *Attorney, Agent, or Firm*—Pepper Hamilton LLP

(57) ABSTRACT

An apparatus and a method for detecting low frequency specular surface flaws on coated substrates is disclosed. A method for detecting low frequency specular surface flaws may comprise: impinging visible electromagnetic radiation or light from an electromagnetic radiation source onto the coated substrate at an oblique angle, reflecting the visible electromagnetic radiation off the coated substrate onto a screen material to form a specular surface flaw reflected image, and recording the reflected image off the screen material with a photosensitive device to form a recorded reflected image.

21 Claims, 4 Drawing Sheets

SPECULAR SURFACE FLAW DETECTION

BACKGROUND

1. Technical Field

The disclosed embodiments generally relate to systems and methods for detecting flaws in coated articles.

2. Description of the Related Art

In the process of electrophotographic imaging, a photoconductive member is electrically charged to a uniform potential. The charged member is exposed to a light image of the original document. The light selectively discharges areas on the surface, while leaving other areas uncharged, thus producing an electrostatic latent image. A developer material, typically containing charged toner particles with opposite polarity as that of the photoconductive member is brought into contact with the exposed photoconductive member. The charged toner particles are transferred to oppositely charged areas on the photoconductive member's surface to form a visible image. An electrostatically charged blank copy sheet is brought into contact with the photoconductive member containing the toner particles, and the toner particles are transferred to the copy sheet. The toner particle image on the blank copy sheet is then heated to permanently affix the toner particles to the sheet to form a "hard copy" image.

Electrophotographic imaging members are well known in the art. An electrophotographic drum is typically used in copiers and printers, and comprises an electrically conductive hollow cylindrical metal substrate in the form of a tube. Typically, the tubes are made from aluminum or other reflective material. To achieve the desired dimensional properties required for these devices, the aluminum tubes are often machined on a lathe and left with a specular or mirror surface, which produces congruent reflection upon exposure to radiation.

The electrophotographic drums of this nature are coated, typically with several layers of coating material, with at least one of which coating layers comprising an organic photoconductive ("OPC") coating. These "layered photoreceptors" have at least a partially transparent photosensitive or photoconductive layer overlying a conductive ground plane, which typically is comprised of the machined mirrored aluminum tube. The layers may be single-layered or multi-layered, such as members having an inner layer of undercoat material and outer layer of change transport material. The tube may be rough or honed, and it may be made of other materials, such as other metals or conductive polymers.

Uniformity of the substrate surface and the coated substrate surface is critical for producing clear images in the electrophotographic process. Uniformity of the outermost transparent or at least partially transparent coating (collectively referred to herein as "transparent coating") is particularly critical for color electrophotographic imaging. Typically, the transparent coating mean thickness may be about 20 µm to about 30 µm. The transparent coating can have coating thickness defects ranging from about 1 µm to about 30 µm. Submicron-sized defects are also possible, while larger defects are possible with thicker coatings.

Coating thickness defects can be in the form of "dimples" which have a coating thickness lower than the mean coating thickness, or "bumps" which have a thickness greater than the mean coating thickness. The coating defects may appear as circumferential banding. When visible electromagnetic radiation, or light, is impinged upon these coating defects at an oblique angle, there is little or no light scattering; the reflection from these coating defects is primarily specular, that is there is a mirror angle reflection. These coating defects in general are referred to as low frequency specular surface flaws due to the subtle nature of the change in coating thickness that accompanies these defects and to the mirror angle specular reflectance of light from these defects.

Low frequency specular surface flaws can be categorized by their thickness difference with respect to the mean coating thickness. For example, in a coating having a thickness of about 25 µm, flaws in the coating on the order of about 1 µm or less may be categorized as Level 0 (zero) flaws; flaws on the order of about 5 µm peak-to-peak (about 1.7 µm peak-to-reference, where reference is the nominal level of the exterior coating) categorized as Level 1 (one) flaws; flaws on the order of about 7.5 µm peak-to-peak (about 5 µm peak-to-reference) may be categorized as Level 2 flaws; and flaws on the order of about 21 µm peak-to-peak (about 18 µm peak-to-reference) may be categorized as Level 3 flaws.

Low frequency specular surface flaws detrimentally affect the performance of the OPC drum photoreceptor in reproducing images. Flaws as small as about 1 µm can have a detrimental effect on the reproduced image. As indicated, the flaws are areas of different coating thicknesses, and as such they have different charging and discharging properties as compared with the flawless areas of the coating and as compared with each other. This typically results in banding on the final image. This is even more critical in high speed color xerographic engines where color registration is critical for true color image reproduction.

Currently, machine vision inspection methods for detecting surface flaws, in general, include dark field angle, use of broad structured light, and laser profiling, for example as taught in U.S. Pat. No. 6,157,450, the disclosure of which is incorporated herein by reference in its entirety. These methods, however, have proved not to be useful in detecting low frequency specular surface flaws on coated substrates. Low frequency specular surface flaws of Level 3 or lower can only currently be observed by manual visual inspection. This method is tedious, inefficient, costly, and time consuming. A cost efficient, automated surface flaw detection means is needed.

Accordingly, there is a need for an improved apparatus and method for detecting low frequency specular surface flaws on coated substrates.

SUMMARY

The disclosure is directed to an apparatus and a method for detecting surface flaws in coated substrates. A method for detecting a low frequency specular surface flaw may comprise: impinging visible electromagnetic radiation or light from an electromagnetic radiation source onto the coated substrate at an oblique angle, reflecting the visible electromagnetic radiation off the coated substrate onto a screen material to form a specular surface flaw reflected image, and recording the reflected image off the screen material with a photosensitive device to form a recorded reflected image.

One embodiment comprises the of use monochromatic light to obtain a specular surface flaw reflected image. Monochromatic light, for purposes herein, consists essentially of visible electromagnetic radiation of one wavelength. In an embodiment of this type, a source of the monochromatic light may be from a laser. Laser light with the wavelength 660 nm or approximately 660 nm is particularly useful, but visible monochromatic light of any wavelength may be used.

In still another embodiment, a fan laser may be used. The fan laser distributes the laser radiation along a line thereby impinging the entire longitudinal extent of a coated substrate. Alternatively, a laser comprising an optic lens system can be used to provide substantially even distribution of the monochromatic light on the coated substrate.

In yet another embodiment, the substrate may be rotated using a motor along a rotational axis, such as a longitudinal axis. In combination with the embodiment using a fan laser or an embodiment comprising an optic lens system to provide even distribution of visible electromagnetic radiation on the coated substrate, rotation of the substrate allows recording a reflected image of the entire longitudinal and circumferential dimensions of the coated substrate, or essentially the entire surface of a three-dimensional object.

In a further embodiment, the photosensitive device used to record the reflected image from the screen material comprises a camera. The camera may be one that records the image on film or it may be of the digital imaging type. It is recognized that any suitably sensitive camera, regardless of how the camera stores or records the image, could be used to record the reflected image from the screen material. In one embodiment, the camera used to record the reflected image off the screen material comprises an area scan charge-coupled device (CCD). In another embodiment, the camera comprises an area scan complementary metal-oxide-semiconductor (CMOS) device.

In still another embodiment the recorded reflected image is digitally processed to determine a dimensional characterization of the specular surface flaws. Factors such as intensity and size of the recorded reflected surface flaws are processed using digital image processing to determine dimensional characteristics such as, but not limited to, flaw heights or depths, and flaw widths and lengths. Digital image processing algorithms are known in the art and any such algorithm know in the art can be adapted in this embodiment.

Yet another embodiment comprises a method for detecting specular surface flaws on a coated organic photoconductor (OPC) drum. This method may include rotating the coated organic photoconductor drum along its drum axis, while impinging visible electromagnetic radiation from a laser onto the OPC drum at an oblique angle The image is reflected off the organic photoconductor drum onto a screen material to form a specular surface flaw reflected image. The reflected image is recorded off the screen material with a camera to form a recorded reflected image. In a further embodiment, the recorded reflected image is subjected to digital image processing to determine flaw dimensional characteristics.

Still yet another embodiment is an apparatus for detecting specular surface flaws on a coated substrate. The apparatus comprises a visible electromagnetic radiation source that impinges visible electromagnetic radiation onto the coated substrate, a screen material for imaging the specular surface flaw reflected image off of the coated substrate, a camera for recording the specular surface flaw reflected image, and a digital processing means to determine a dimensional characterization of the specular surface flaws.

One embodiment of the apparatus comprises a laser. A laser that emits light with a wavelength 660 nm is particularly preferred embodiment, but other embodiments use a laser that emits visible monochromatic light of any wavelength.

In still another embodiment of the apparatus comprises a fan laser. In yet another embodiment of the apparatus, a laser comprising an optic lens system is used to provide even distribution of the monochromatic light on the coated substrate.

In yet another embodiment, the apparatus comprises a rotation means for rotating the substrate along a rotational axis, such as a longitudinal axis.

The camera of the apparatus of one embodiment comprises an area scan charge-coupled device (CCD). In another embodiment, the camera comprises an area scan complementary metal-oxide-semiconductor (CMOS) device. The camera of the apparatus may comprise any suitably sensitive film-type or digital imaging camera.

DETAILED DESCRIPTION

Before the present methods, systems and materials are described, it is to be understood that this disclosure is not limited to the particular methodologies, systems and materials described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. Nothing herein is to be construed as an admission that the embodiments described herein are not entitled to antedate such disclosure by virtue of prior invention.

Figure 1:
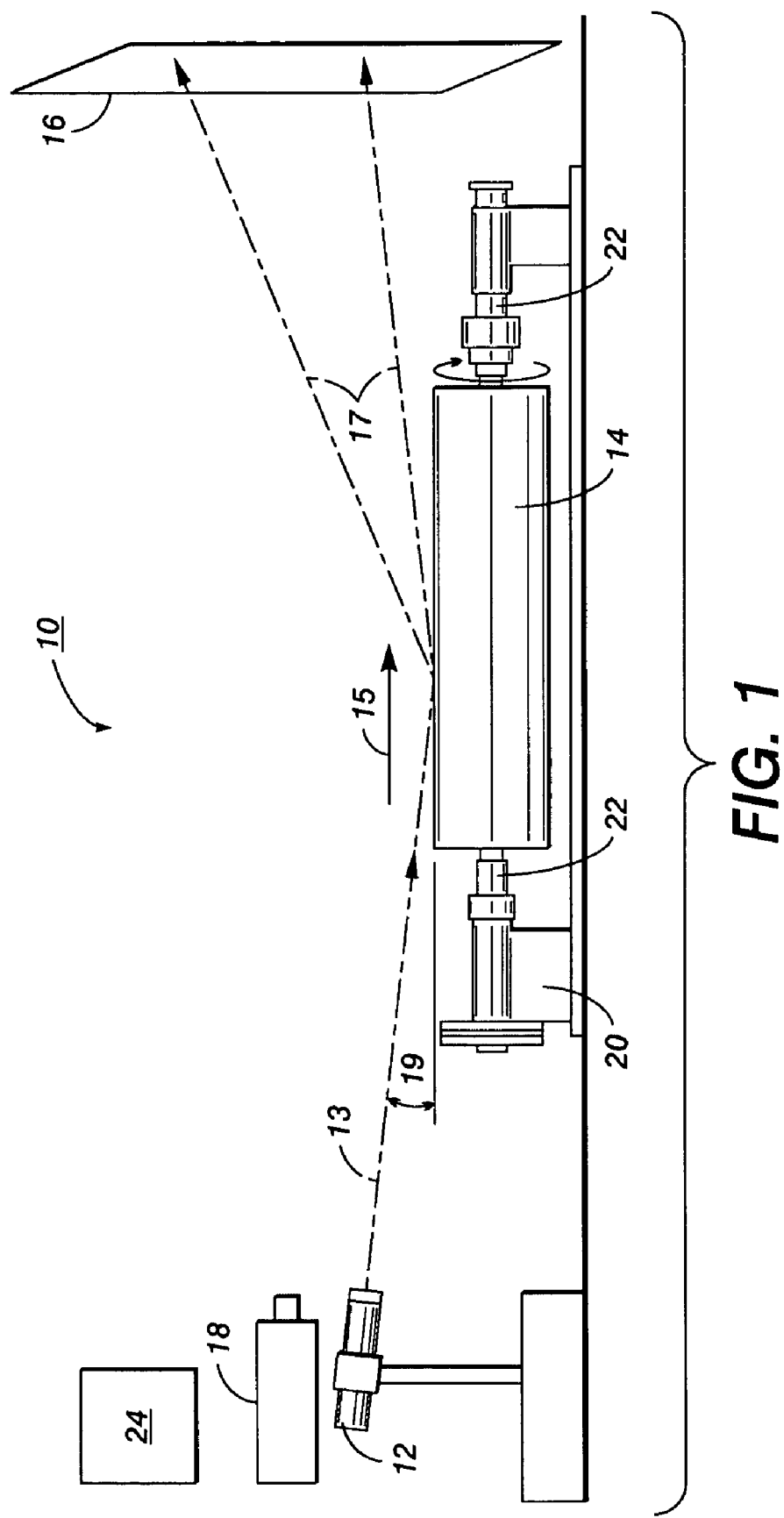
FIG. 1 illustrates exemplary apparatus for detecting low frequency specular surface flaws.

In accordance with one embodiment, as illustrated in FIG. 1 an apparatus 10 to detect low frequency specular surface flaws is depicted. The apparatus 10 comprises a laser 12. The laser 12 may comprise a fan laser, which illuminates a line or stripe of laser light on the at least partially transparently coated substrate 14 or a laser comprising an optic lens system (not shown) to provide even distribution of visible electromagnetic radiation on the partially transparently coated substrate 14. In an embodiment, a coated substrate 14 may include a rotational axis 15. The laser 12 emits light 13 at an oblique angle 19 with respect to the partially transparently coated substrate surface. One embodiment may use an oblique angle of the laser light with respect to the coated substrate 14 surface of about 1° to about 80°. Another embodiment may uses an oblique angle for the light of about 3° to about 45°. Yet another embodiment may uses an oblique angle of about 9°.

The apparatus of this embodiment further comprises a screen material 16. The screen material 16 may comprise any flat or nearly flat, white or nearly white material that yields a sharp image of the specular surface flaw reflected image, such as cloth or other textiles, matte white fiberglass, vinyl or other material. A suitably sensitive camera 18 is provided to record the surface flaw reflected image off of the screen material 16. The camera 18 may be of the film-type, which typically use emulsion photographic films to capture images, or of the digital type. A camera in one embodiment may comprise a charge-coupled device (CCD) area scan camera. Another embodiment for the suitably sensitive camera 18 comprises an area scan complementary metal-oxide-semiconductor (CMOS) device.

In one specific example, when a coated substrate comprised a 357 mm long OPC drum, a laser was positioned 7¾ inches from an end of the drum to direct a laser toward the drum at an approximately 20° angle. The screen was positioned 18 inches from the other end of the drum.

Optionally the apparatus further comprises a coated substrate rotating means 20. The rotating means may comprise an electric motor integrally attached to a coated substrate suspending member 22. The coated substrate 14 is affixed to the coated substrate suspending member 22 and rotated during illumination to reflect light 17 toward the screen and provide a specular surface flaw reflected image on the screen material 16. It is recognized that a rotating means other than an electric motor, for example but not limited to, a battery operated motor, are effective for the apparatus 10 to detect low frequency specular surface flaws. In an embodiment that comprises the use of the apparatus to detect low frequency specular surface flaws on a coated substrate which comprises an OPC drum, a rotation speed of the drum may be about 1 revolution per minute (rpm) to about 100 rpm. In another embodiment, a rotation speed may be about 40 rpm to about 60 rpm. In another embodiment, a rotation speed of the drum may be about 50 rpm. It should be recognized that faster rotation speeds of the coated substrate may expedite the flaw detection, and that the rotation speed is currently only limited by the camera frame rate and the number of pixels available for digital image processing. However, it should also be recognized that rotation is not required to practice the embodiments described herein, and the methods described may be used on coated cylindrical objects, coated flat objects, or other surfaces.

Figure 2:
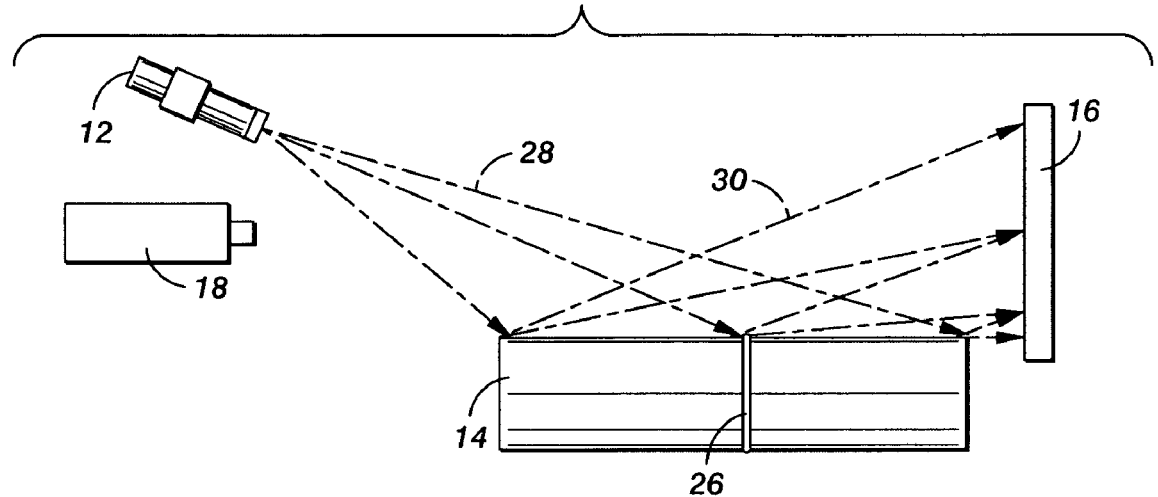
FIG. 2 depicts exemplary method using a fan laser to illuminate a length of coated substrate and reflecting a specular surface flaw image onto a screen material.

Now referring to FIG. 2, an embodiment of the method for detecting low frequency specular surface flaws 26 on a coated substrate 14, which for this example comprises an OPC coated drum, is depicted. The coated substrate 14 is optionally rotated with a rotating means 20 (not shown in FIG. 2). A line of visible electromagnetic radiation 28 is emitted from a laser 12. In the embodiment shown this may be achieved using a fan laser or a laser comprising an optic lens system to provide even distribution of visible electromagnetic radiation 28 on the coated substrate 14. Visible electromagnetic radiation 28 with a wavelength of approximately 660 nm used in various embodiments, but it is recognized that any wavelength of visible light will work for this invention. In some embodiments, a narrow bandwidth laser of about 29 nm (+/−3%) may be used. The visible electromagnetic radiation 28 reflects off of the coated substrate 14 as reflected electromagnetic radiation 30 to form a specular surface flaw reflected image on the screen material 16. Low frequency specular surface flaws 26 are represented in the specular surface flaw reflected image in differences in contrast from the flawless coating area. The specular surface flaw reflected image on the screen material 16 is recorded using a suitably sensitive camera 18 and the image may be digitally processed using a computer (not shown) and digital imaging processing software, which are known to persons having ordinary skill in the art.

Figure 3:
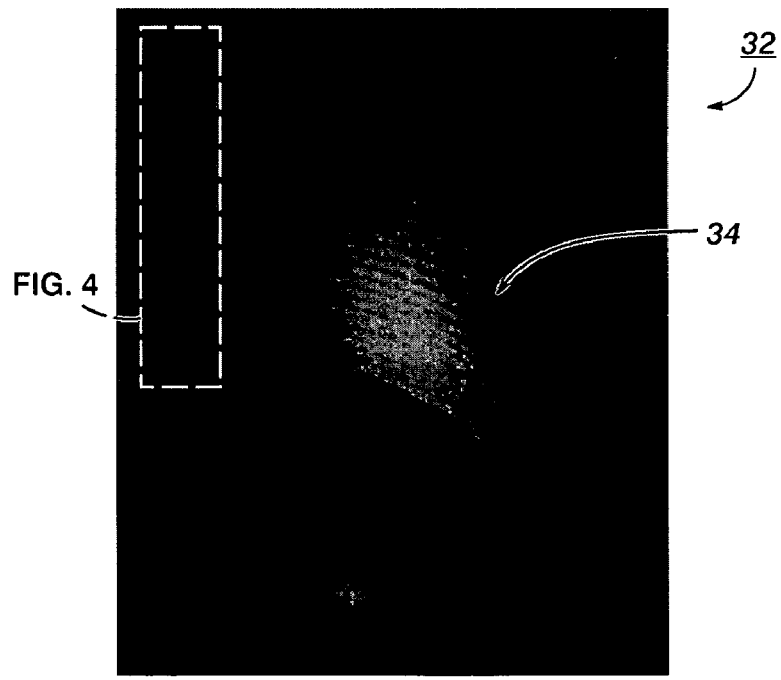
FIG. 3 is a reflected specular surface flaw image recorded from the screen material off an organophotoconductor drum as practiced in one embodiment.

Now referring to FIG. 3, a black and white reproduction of a specular surface flaw reflected image 32 from a coated substrate 14 comprising an OPC drum is presented. The surface flaws 34 in the specular surface flaw reflected image 32 appear as areas of varying contrast, and for this case have a periodic band nature. The flaws 34 appear in the image due to differences in interference of the reflected electromagnetic radiation 30 from flawed and flawless 38 areas. The use of the screen material 16 to form the specular surface flaw reflected image 32 is important for the disclosed embodiments. Attempting to directly record the specular surface flaw reflected image with a suitably sensitive camera (i.e., reflecting the light directly into the camera with no reflective screen) does not result in the detection of flaws on the small size levels described herein. Thus, the present embodiments assist in the detection of smaller coating surface flaws than were previously possible.

Figure 5:
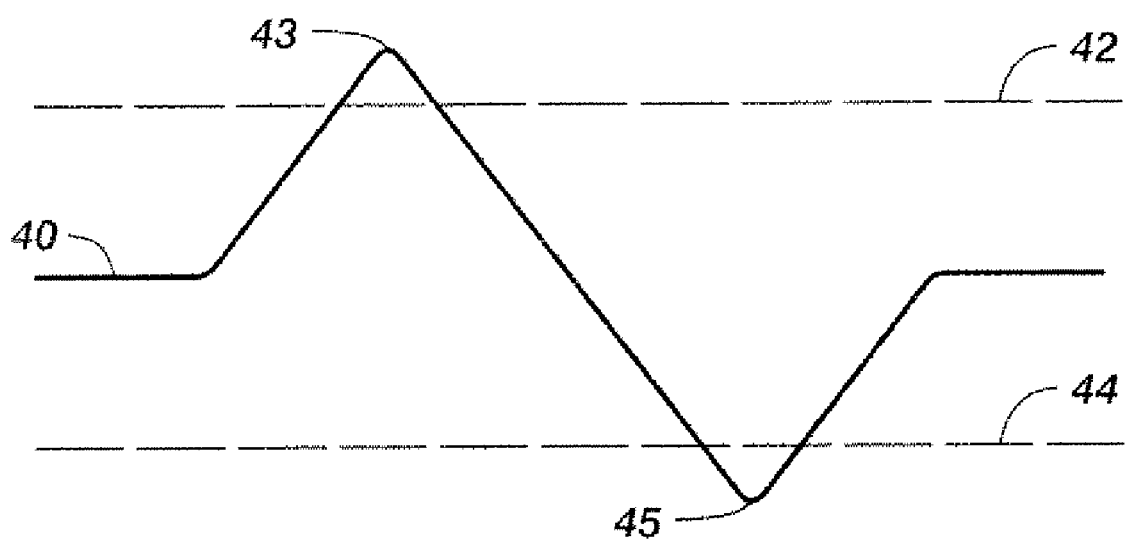
FIG. 5 illustrates an exemplary image processing method.

Using a suitably sensitive camera 18 to record the specular surface flaw reflected image 34 off a screen material 16 may provide detection of flaws down to the size of Level 0, or 1 µm or less. Flaw detection may then occur using any suitable image processing technique to detect variations in the captured image. For example, referring to FIG. 5, a portion of the reflected image may be processed on a pixel-by-pixel basis, and flaws may be indicated by measuring an intensity level 40 for each pixel. If a pixel intensity level exceeds an upper threshold 42 it may indicate a defect 43. Similarly, if a pixel intensity level is lower than a lower threshold 44, it may indicate a defect 45.

Figure 4:
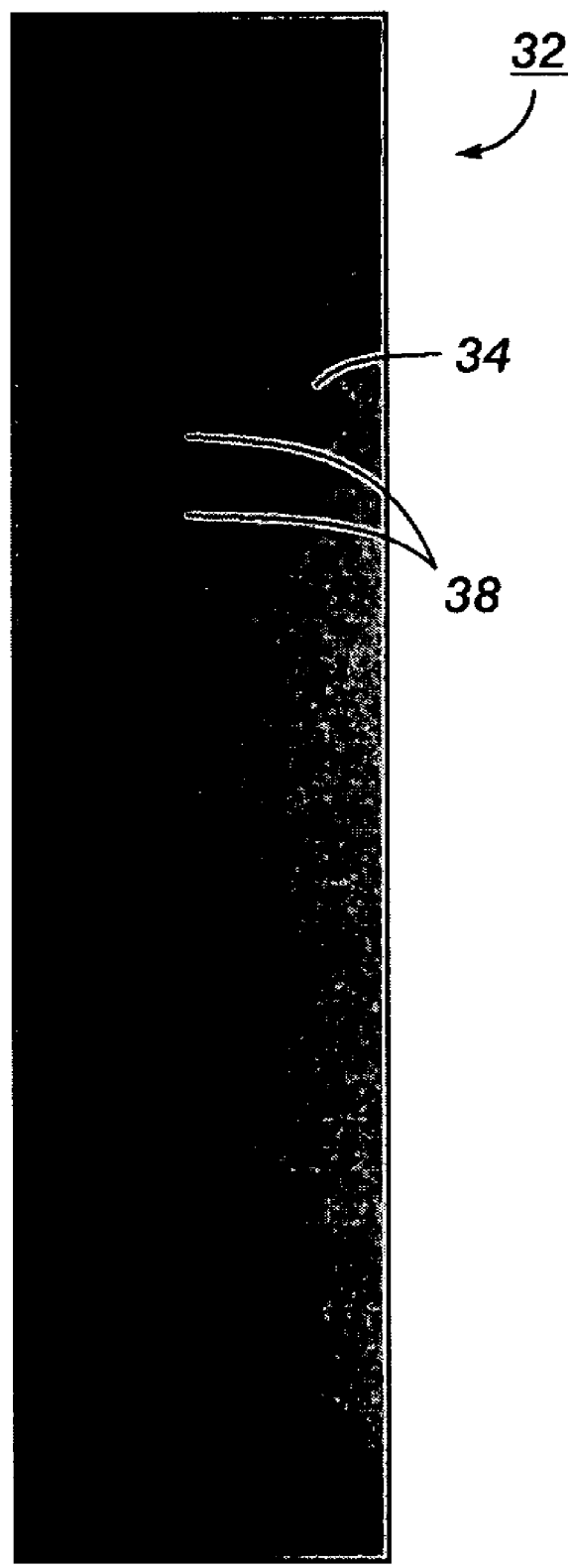
FIG. 4 is a blow-up of the reflected specular surface flaw image depicted in FIG. 3.

In various embodiments, coating thickness measurements using, for example, a Permascope and form gauge revealed that the height of these specular surface flaws 34 or defects depicted in the specular surface flaw reflected images of FIGS. 3 and 4 was on the order of 0.75 µm, that is, Level 0 defects.

It will also be recognized that the embodiments described herein may be used on various substrates with transparent coatings. For example, an OPC drum may be coated with any suitable coating or coatings to fabricate a photosensitive imaging member. Such coatings my include multi-layer coatings, such as a barrier uncoat material (UCM) may be applied, along with a charge generating material (CGM) and a charge transport material (CTM). The CGM and CTM may be in different layers or in a single layer along with a binder resin. Typical organic photoconductive CGMs include, for example, one or more of azo pigments, such as Sudan Red, Dian Blue, Janus Green B, and the like; quinone pigments such as Algol Yellow, Pyrene Quinone, Indanthrene Brilliant Violet RRP, and the like; quinocyanine pigments; perylene pigments; indigo pigments such as indigo, thioindigo, and the like; bisbenzoimidazole pigments such as Indofast Orange toner, and the like; phthalocyanine pigments such as copper phthalocyanine, aluminochloro-phthalocyanine, titanyl phthalocyanine, hydroxy gallium phthalocyanine and the like; quinacridone pigments; or azulene compounds. Typical inorganic photoconductive CGMs include, for example, cadmium sulfide, cadmium sulfoselenide, cadmium selenide, crystalline and selenium, lead oxide and other chalcogenides.

Typical CTMs include, for example, one or more organic polymer or non-polymeric materials capable of supporting the injection of photoexcited holes or transporting electrons from the photoconductive material and allowing the transport of these holes or electrons through the organic layer to selectively dissipate a surface charge. Typical CTMs may also include, for example, a positive hole transporting material selected from compounds having in the main chain or the side chain a polycyclic aromatic ring such as anthracene, pyrene, phenanthrene, coronene, and the like, or a nitrogen-containing hetero ring such as indole, carbazole, oxazole, isoxazole, thiazole, imidazole, pyrazole, oxadiazole, pyrazoline, thiadiazole, triazole, hydrazone compounds, and the like. Other typical CTMs may include electron donor materials, such as carbazole; N-ethyl carbazole; N-isopropyl carbazole; N-phenyl carbazole; tetraphenylpyrene; 1-methyl pyrene; perylene; chrysene; anthracene; tetraphene; 2-phenyl naphthalene; azopyrene; 1-ethyl pyrene; acetyl pyrene; 2,3-benzochrysene; 2,4-benzopyrene; 1,4-bromopyrene; poly(N-vinylcarbazole); poly(vinylpyrene); poly(vinyltetraphene); poly(vinyltetracene), poly(vinylperylene), and the like. Typical electron transport materials include, for example, electron acceptors such as 2,4,7-trinitro-9-fluorenone; 2,4,5,7-tetranitro-fluorenone; dinitroanthracene; dinitroacridene; tetracyanopyrene, dinitroanth like. The CTM may also incorporate an antioxidant such as butylated hydroxyl toluene to inhibit oxidation and deterioration of the CTM. The CTM may also incorporate poly(tetrafluoroethylene) (PTFE) in order to reduce wear and enable more efficient toner transfer.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for detecting a coating thickness defect on a coated substrate, comprising:
   impinging visible electromagnetic radiation from an electromagnetic radiation source onto a coated substrate at an oblique angle; wherein the coated substrate comprises at least one coating thickness defect, and wherein the at least one coating thickness defect has a coating thickness difference of about 18 μm or less compared to a nominal coating thickness;
   reflecting the visible electromagnetic radiation off the at least one coating thickness defect in a substantially specular direction onto a screen material to form a coating thickness defect specular reflected image wherein the coating thickness defect specular reflected image comprises an area of different contrast compared with a flawless coating area; and
   recording the specular reflected image off the screen material with a photosensitive device to form a recorded coating thickness defect specularly reflected image.

2. The method of claim 1 wherein the coating is at least partially transparent.

3. The method of claim 1 wherein the coated substrate comprises an organic photoconductor.

4. The method of claim 1 wherein the coated substrate is rotated about a rotational axis.

5. The method of claim 1 wherein the visible electromagnetic radiation source comprises a laser.

6. The method of claim 5 wherein the laser comprises an optic lens system to provide substantially even distribution of visible electromagnetic radiation on the coated substrate.

7. The method of claim 1, further comprising digitally processing the recorded image to determine a dimensional characterization of the at least one coating thickness defect.

8. The method of claim 1, wherein the at least one coating thickness defect has a coating thickness difference of about 5 μm or less compared to a nominal coating thickness.

9. The method of claim 1, wherein the coating thickness defect reflected image corresponds to a coating thickness defect of about 1.7 μm compared to a nominal coating thickness.

10. The method of claim 1, wherein the coating thickness defect has a peak to peak coating thickness difference of about 21 μm or less compared to a nominal coating thickness.

11. The method of claim 1, wherein the coating thickness defect is 1 μm or less.

12. The method of claim 7, wherein the processing comprises:
    measuring an intensity level for a plurality of pixels in the recorded image; and
    determining that a defect exists if a pixel intensity level either exceeds an upper threshold or is lower than a lower threshold.

13. A method, comprising:
    rotating a coated organic photoconductor drum along a drum axis; wherein the coated organic photoconductor further comprises at least one coating thickness defect, and wherein the at least one coating thickness defect has a coating thickness difference of about 18 μm or less compared to a nominal coating thickness;
    impinging visible electromagnetic radiation from a laser onto the drum at an oblique angle;
    reflecting the visible electromagnetic radiation off the drum in a substantially specular direction onto a screen material to form a coating thickness defect specularly reflected image, wherein the coating thickness defect specular reflected image comprises an area of different contrast compared with a flawless coating area; and
    recording the reflected image off the screen material with a photosensitive device to form a recorded coating thickness defect specularly reflected image.

14. The method of claim 13 further comprising digitally processing the recorded image to determine a dimensional characterization of the at least one coating thickness defect.

15. The method of claim 13 wherein the laser comprises an optic lens system to provide substantially even distribution of visible electromagnetic radiation on the coated substrate.

16. The method of claim 13 wherein the coating thickness defect specularly reflected image corresponds to a coating thickness defect of about 1 μm to about 30 μm.

17. The method of claim 13 wherein the coating thickness defect specular reflected image corresponds to a coating thickness defect of about 0.75 μm compared to a nominal coating thickness.

18. An apparatus, comprising:
    a visible electromagnetic radiation source, wherein the electromagnetic radiation source impinges visible electromagnetic radiation onto the coated substrate;
    a screen material for imaging at least one coating thickness defect specularly reflected image off of the coated substrate, wherein the at least one coating thickness defect has a coating thickness difference of about 18 μm or less compared to a nominal coating thickness, and wherein the coating thickness defect specularly reflected image comprises an area of different contrast compared with a flawless coating area;

a photosensitive device for recording the coating thickness defect specularly reflected image, wherein the photosensitive device produces a recorded coating thickness defect specularly reflected image; and a digital processing system to determine a dimensional characterization of a coating thickness defect from the recorded coating thickness defect specularly reflected image.

19. The apparatus of claim 18 further comprising a motor that rotates the coated substrate along a rotational axis of the substrate.

20. The apparatus of claim 18 wherein the visible electromagnetic radiation source comprises a laser.

21. The apparatus of claim 18 wherein the laser comprises an optic lens system to provide substantially even distribution of visible electromagnetic radiation on the coated substrate.

* * * * *